United States Patent
Bosset et al.

(10) Patent No.: US 12,111,429 B2
(45) Date of Patent: Oct. 8, 2024

(54) DIGITAL DETECTOR WITH SUPERPOSED CONVERSION STAGES

(71) Applicant: TRIXELL, Moirans (FR)

(72) Inventors: Bruno Bosset, Moirans (FR); Thierry Ducourant, Moirans (FR); Bruno Commere, Moirans (FR)

(73) Assignee: TRIXELL, Moirans (FR)

( * ) Notice: Subject to any disclaimer, the term of this patent is extended or adjusted under 35 U.S.C. 154(b) by 212 days.

(21) Appl. No.: 17/669,316

(22) Filed: Feb. 10, 2022

(65) Prior Publication Data
US 2022/0252740 A1 Aug. 11, 2022

(30) Foreign Application Priority Data
Feb. 11, 2021 (FR) ........................................ 2101326

(51) Int. Cl.
*G01T 1/20* (2006.01)
*A61B 6/42* (2024.01)
*H01L 27/146* (2006.01)
*H04N 5/32* (2023.01)

(52) U.S. Cl.
CPC ........ *G01T 1/20184* (2020.05); *A61B 6/4233* (2013.01); *G01T 1/20181* (2020.05); *H01L 27/14663* (2013.01); *H04N 5/32* (2013.01)

(58) Field of Classification Search
CPC .............. A61B 6/4233; G01T 1/20181; G01T 1/20184; H01L 27/14663; H04N 5/32
See application file for complete search history.

(56) References Cited

U.S. PATENT DOCUMENTS

| | | | | |
|---|---|---|---|---|
| 4,905,265 A | * | 2/1990 | Cox ...................... | G01T 1/2928 378/19 |
| 4,945,242 A | * | 7/1990 | Berger ................. | H04N 5/3205 250/370.06 |
| 5,043,582 A | * | 8/1991 | Cox .................. | H01L 27/14663 250/336.1 |

(Continued)

FOREIGN PATENT DOCUMENTS

| EP | 2 708 023 B1 | 6/2019 |
|---|---|---|
| EP | 3 672 230 A1 | 6/2020 |

*Primary Examiner* — Blake C Riddick
(74) *Attorney, Agent, or Firm* — Baker Hostetler (57) ABSTRACT

A digital detector includes a conversion block intended to convert incident radiation into electric charge; an electronic card that converts the electric charge into a digital image, the conversion block comprising N conversion stages superposed on one another, N being an integer between 2 and M, each of the N conversion stages comprising: a monolithic substrate; a first converter assembly in the form of a polygonal matrix array, M being the number of sides of the polygonal matrix array, M preferably being equal to 4, and configured so as to generate the electric charge on the basis of the incident radiation; an addressing and driving module for addressing and driving the matrix array, the addressing and driving module being arranged on the monolithic substrate along one side of the polygonal matrix array; each of the N conversion stages being oriented by at least 1/M of a turn with respect to the other N−1 conversion stages of the conversion block, and with an orientation distinct from the other N−1 conversion stages of the conversion block.

9 Claims, 5 Drawing Sheets

(56) References Cited

U.S. PATENT DOCUMENTS

| | | | | |
|---|---|---|---|---|
| 5,381,013 A * | 1/1995 | Cox | ...................... | H04N 3/155 348/E3.018 |
| 5,440,130 A * | 8/1995 | Cox | ................. | H01L 27/14618 348/E3.018 |
| 5,464,984 A * | 11/1995 | Cox | ................. | H01L 27/14663 348/E3.018 |
| 6,035,013 A * | 3/2000 | Orava | ............... | H01L 27/14676 348/E3.018 |
| 6,243,441 B1 * | 6/2001 | Zur | .......................... | G01T 1/24 378/98.7 |
| 2001/0038076 A1 * | 11/2001 | Kuwabara | ............. | G01T 1/2928 250/366 |
| 2002/0079458 A1 * | 6/2002 | Zur | ...................... | G01T 1/2928 250/370.11 |
| 2002/0110216 A1 * | 8/2002 | Saito | .................... | G01N 23/046 378/19 |
| 2003/0010923 A1 * | 1/2003 | Zur | ........................ | G01T 1/247 348/E5.086 |
| 2003/0015664 A1 * | 1/2003 | Agano | ..................... | H04N 5/32 348/E5.086 |
| 2003/0164888 A1 * | 9/2003 | Orava | ............... | H01L 27/14676 348/E3.018 |
| 2003/0226898 A1 * | 12/2003 | Chen | ...................... | G06K 19/07 235/492 |
| 2004/0000630 A1 * | 1/2004 | Spartiotis | ............. | G01T 1/2964 250/208.1 |
| 2004/0004189 A1 * | 1/2004 | Brahme | .................... | G01T 1/24 250/370.08 |
| 2004/0146138 A1 * | 7/2004 | Jiao | .................... | G01T 1/20183 378/19 |
| 2004/0200971 A1 * | 10/2004 | De Keyser | ............. | G01N 23/04 378/98.8 |
| 2005/0199819 A1 * | 9/2005 | Wieczorek | ................ | G01T 1/20 250/370.11 |
| 2006/0027760 A1 * | 2/2006 | Rougeot | ........... | H01L 27/14658 250/370.09 |
| 2006/0192087 A1 * | 8/2006 | Kuszpet | ................. | G01T 1/247 250/214 R |
| 2007/0096031 A1 * | 5/2007 | Meier | ................. | G01T 1/20185 250/370.11 |
| 2007/0211858 A1 * | 9/2007 | Franklin | ........... | H01L 27/14676 378/97 |
| 2008/0240339 A1 | 10/2008 | Du et al. | | |
| 2008/0245968 A1 * | 10/2008 | Tredwell | ............. | G01T 1/20183 250/370.09 |
| 2009/0290680 A1 * | 11/2009 | Tumer | .................... | G01T 1/249 250/311 |
| 2010/0079649 A1 * | 4/2010 | Ayraud | ................. | H04N 25/709 348/308 |
| 2010/0104067 A1 * | 4/2010 | Okada | ....................... | G01T 1/00 378/62 |
| 2010/0187429 A1 * | 7/2010 | Engel | .................... | G01T 1/2928 250/370.09 |
| 2011/0024642 A1 * | 2/2011 | Tredwell | ............... | G01T 1/2019 438/66 |
| 2011/0226951 A1 * | 9/2011 | Kammerer | ............ | G01T 1/2985 250/336.1 |
| 2011/0303849 A1 * | 12/2011 | Tredwell | ............. | G01T 1/20184 250/362 |
| 2012/0081589 A1 * | 4/2012 | Nishihara | .............. | H04N 25/57 348/308 |
| 2012/0097858 A1 | 4/2012 | Morf | | |
| 2013/0009067 A1 * | 1/2013 | Schmand | .............. | G01T 1/1642 250/366 |
| 2013/0119260 A1 * | 5/2013 | Nakatsugawa | ...... | A61B 6/4208 250/366 |
| 2013/0170616 A1 * | 7/2013 | Mruthyunjaya | ....... | G01N 23/04 438/69 |
| 2014/0246596 A1 * | 9/2014 | Antonuk | ........... | H01L 27/14658 250/369 |
| 2014/0321618 A1 * | 10/2014 | Blanchon | ................ | G01T 1/172 378/91 |
| 2015/0144796 A1 * | 5/2015 | Tredwell | ................. | H01L 31/18 438/69 |
| 2015/0177390 A1 * | 6/2015 | Mattson | .................... | G01T 1/00 250/366 |
| 2015/0303228 A1 * | 10/2015 | Rohr | ...................... | H01L 31/032 250/366 |
| 2016/0216381 A1 * | 7/2016 | Nishihara | ............. | G01T 1/2002 |
| 2016/0241805 A1 * | 8/2016 | Nishihara | ............ | H04N 25/772 |
| 2016/0286146 A1 * | 9/2016 | Wirth | ................ | H01L 27/14636 |
| 2017/0194375 A1 * | 7/2017 | Jacob | ................ | H01L 27/14689 |
| 2017/0229502 A1 * | 8/2017 | Liu | ................... | H01L 27/14676 |
| 2018/0020997 A1 * | 1/2018 | Fujita | ................... | A61B 6/4233 378/62 |
| 2018/0331137 A1 * | 11/2018 | Jacob | .................... | H04N 25/771 |
| 2019/0388042 A1 * | 12/2019 | Zhao | ......................... | G01T 1/20 |
| 2020/0116875 A1 * | 4/2020 | Nishihara | ........... | G01T 1/20184 |
| 2020/0124749 A1 * | 4/2020 | Takenaka | ............ | G01T 1/20183 |
| 2020/0204754 A1 * | 6/2020 | Marecaux | ............. | H04N 25/77 |
| 2020/0264319 A1 * | 8/2020 | Takenaka | ............ | G01T 1/2002 |
| 2021/0356608 A1 * | 11/2021 | Jacobs | ................. | G01T 1/2985 |
| 2022/0050218 A1 * | 2/2022 | Jacobs | ...................... | G01T 1/20 |
| 2022/0075085 A1 * | 3/2022 | Kawanabe | .......... | G01T 1/20187 |
| 2022/0196857 A1 * | 6/2022 | Kawanabe | ............ | H04N 25/75 |
| 2023/0168391 A1 * | 6/2023 | Boucher | ............... | H04N 25/778 378/62 |

* cited by examiner

DIGITAL DETECTOR WITH SUPERPOSED CONVERSION STAGES

CROSS-REFERENCE TO RELATED APPLICATIONS

This application claims priority to foreign French patent application No. FR 2101326, filed on Feb. 11, 2021, the disclosure of which is incorporated by reference in its entirety.

FIELD OF THE INVENTION

The invention lies in the technical field of medical imaging, and more precisely in that of digital image sensors for radiology. It relates to a digital detector with superposed conversion stages.

BACKGROUND

A traditional image detector typically comprises a planar sensor comprising a set of pixels organized into a matrix array in rows and columns, row addressing blocks, column readout blocks, row conductors connecting the rows of pixels to a row addressing block, and column conductors connecting the columns of pixels to a column readout block. It should be noted that, in the context of the present patent application, the concepts of column and row have only a relative meaning, with a row of pixels and a column of pixels being nothing more than rows of pixels that are arranged for example, and without limitation, perpendicularly to one another. A row conductor, respectively column conductor, is defined as being oriented parallel to a row of pixels, respectively a column of pixels.

Figure 1:
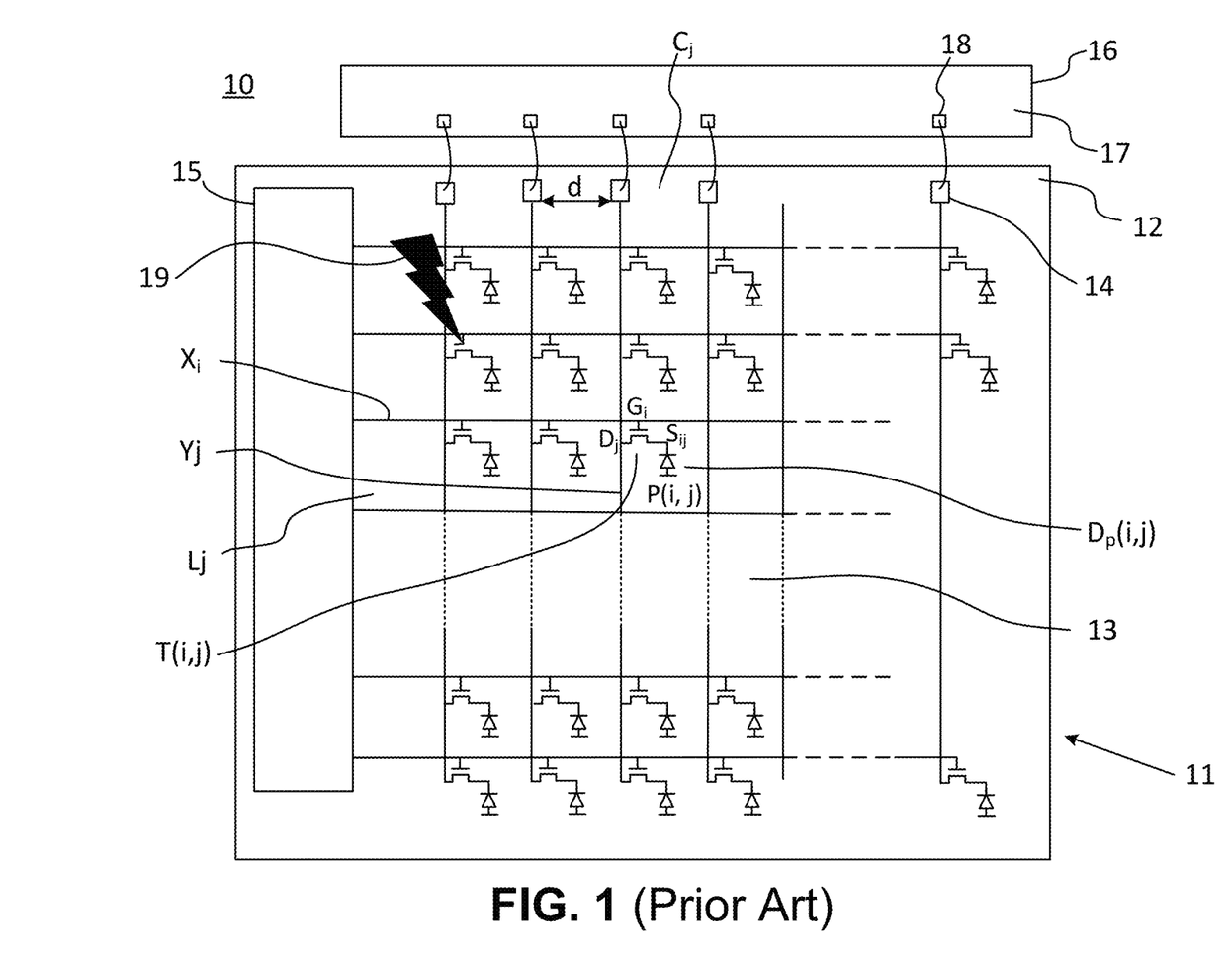
FIG. 1 schematically shows a traditional image detector.

FIG. 1 shows a traditional image detector 10. The image detector 10 comprises a sensor 11 formed on a first monolithic substrate 12. The first monolithic substrate 12 comprises a set of pixels P(i,j) organized into a matrix array 13 in rows Li and columns Cj. The matrix array 13 may contain any number of rows and columns thus forming pixels P(i,j). The matrix array 13 forms a geographical region on the first substrate 12. The pixels are denoted in the generic form P(i,j), where i and j are natural integers denoting the rank of the row and the rank of the column in the matrix array 13, respectively. The set of pixels P(i,j) is configured so as to generate signals on the basis of radiation impinging on the detector 10. More precisely, incident radiation 19 is converted into a light signal by a scintillator, and it is this light signal that is processed by the set of pixels. The sensor 11 comprises column conductors Yj, each connecting the pixels of a given column Cj. The column conductors Yj are intended to carry the signals generated by the pixels P(i,j). Likewise, the sensor 11 comprises row conductors Xi, each connecting the pixels of a given row Li. The matrix array 13 of pixels P(i,j) comprises columns Cj. Likewise, the matrix array 13 of pixels P(i,j) comprises rows Li. The sensor 10 comprises contact pads 14 located at the periphery of the first substrate 12 and outside of the matrix array 13 of pixels P(i,j). The contact pads 14 are connected to the column conductors Yj. The image detector 10 comprises a row addressing block 15 located close to the first substrate 12 and connected to the row conductors Xi. Row addressing block 15 is the name given to any assembly comprising at least one row addressing block. The block 15 may be integrated into the first substrate 12, as shown in FIG. 1, or else integrated into a different substrate. The row addressing block 15 makes it possible to address each row of pixels Li individually. The image detector 10 comprises a column readout block 16 that is generally formed on a second substrate 17 different from the first substrate 12. The column readout block 16 comprises connection points 18 that connect the column readout block 16 to the contact pads 14. The column readout block 16 makes it possible to read out the signals generated by the pixels of the row selected by the row addressing block.

A pixel P(i,j) comprises a photodiode Dp(i,j) associated with an electronic switch T(i,j). The photodiodes Dp(i,j) may of course be replaced with any photosensitive element able to generate an electrical signal when it is subjected to photon radiation. The pixel structure shown in FIG. 1 is intentionally simplified, and more complex structures may be implemented within the scope of the invention.

The switch T(i,j) formed by a transistor is connected by its gate Gi to the row conductor Xi of the row i, by its drain Dj to the column conductor Yj and by its source Sij to the cathode of the photodiode Dp(i,j). The anodes of all of the photodiodes Dp(i,j) are connected to a common potential, for example ground. The row addressing block 15 comprises elements for generating the signals to be injected onto the row conductors Xi in order to drive the opening and closing of the transistors T(i,j). The column readout block 16 may comprise elements for processing the signals received on the column conductors Yj. These may in particular be an amplifier and/or an analogue-to-digital converter.

The image sensor 11 traditionally operates as follows. In an image capturing phase, the exposure of the photodiodes Dp(i,j) to radiation generates electric charge at the source Sij. The amount of charge at each source Sij depends on the intensity of the radiation received by the pixel P(i,j) under consideration. The image capturing phase is followed by a readout phase, performed row by row. The signals injected onto the various row conductors Xi move successively to the active state, such that the potential of each column conductor Yj is successively representative of the amount of electric charge accumulated in the various pixels P(i,j) of the column j.

It should be noted that, in this example and by way of illustration, the conversion of the incident radiation into electric charge is performed by a scintillator and photodiodes. Reference may be made to a conversion stage. Such a conversion stage for converting incident radiation into electric charge may be obtained with a photodetector.

In order to obtain greater sensitivity to the X-ray radiation to which the detector is subjected, it is known to stack multiple matrix arrays and multiple scintillators. Specifically, stacking multiple matrix arrays and multiple scintillators makes it possible to create sensors that offer energy resolution for the X-ray image by separating the lowest-energy radiation, which is absorbed in the upper layers of the scintillator, and the highest-energy radiation, which is absorbed in the lower layers.

Combining and expediently designing one or more scintillators and one or more matrix arrays of photodiodes thus makes it possible to create images in which radiation having different energies is separated, in the same way as "colour" images in the field of cameras and television sets operating in the visible range. In the most common arrangement, sensors offering this spectral resolution consist of two matrix arrays of photodiodes associated with one or more scintillating layers.

Although existing devices that have already been described offer a wide variety of structures and stacks, little or no description is given of the addressing and readout means for addressing and reading out the matrix arrays.

However, this connection to the outside is essential in order to be able to read out the signal generated at the pixels and transmit an electronic signal that allows the construction of a digital image. In the most common arrangements from the prior art, the addressing and the readout are performed on two perpendicular edges of the matrix array, the addressing usually being performed in rows and the readout in columns.

Although two edges are necessary for the driving and the readout of each matrix array of pixels, as has been shown in the exemplary detector from the prior art of FIG. 1, it becomes clear that a square or rectangular spectral imaging device may be implemented relatively easily by stacking two matrix arrays and thus using the four sides of the stack for the functions of driving and reading out the two matrix arrays. However, if the stack comprises more than two matrix arrays of photodiodes, this connection becomes far trickier and requires complex architectures. Implementation becomes very difficult if the sensor is additionally constrained in terms of thickness, such as for example in the case of portable detectors that have to fit within a template of standardized dimensions.

SUMMARY OF THE INVENTION

The invention aims to overcome all or some of the problems cited above by proposing a radiology image detector that makes it possible to maximize the absorption of X-rays, the spatial and spectral resolution of the image and the selectivity between the various energies, while still remaining compact. Such a detector makes it possible to obtain stacks that may comprise a plurality of matrix arrays of photodiodes and potentially twice as many scintillating layers, while still retaining the possibility of easily driving and reading out the matrix arrays.

To this end, one subject of the invention is a digital detector comprising:
- a conversion block intended to convert incident radiation into electric charge;
- an electronic card that converts the electric charge into a digital image, characterized in that the conversion block comprises N conversion stages superposed on one another, N being an integer between 2 and M, each of the N conversion stages comprising:
- a monolithic substrate;
- a first converter assembly in the form of a polygonal matrix array, M being the number of sides of the polygonal matrix array, M preferably being equal to 4, said matrix array being arranged on the monolithic substrate and being organized in rows and columns and configured so as to generate the electric charge on the basis of the incident radiation; an addressing and driving module for addressing and driving the matrix array, said addressing and driving module being arranged on the monolithic substrate at the base of the columns along one side of the polygonal matrix array, and intended to address the rows and transport the generated electric charge in the columns;

and in that each of the N conversion stages is oriented by at least 1/M of a turn with respect to the other N−1 conversion stages of the conversion block, and with an orientation distinct from the other N−1 conversion stages of the conversion block.

In one embodiment of the invention, said converter assemblies are photodetectors, each of the photodetectors being able to absorb the incident radiation and to transform it into electric charge.

Advantageously, at least one of the N conversion stages furthermore comprises a second converter assembly arranged underneath the monolithic substrate of said at least one of the N conversion stages.

Advantageously, the digital detector according to the invention furthermore comprises a filter for filtering the predetermined-energy incident radiation between the second converter assembly of the at least one of the N conversion stages and the first converter assembly of the lower conversion stage.

In another embodiment of the invention, each of said converter assemblies comprises a first scintillator able to convert the incident radiation into a light signal, and the polygonal matrix is a matrix array of pixels and configured so as to generate the electric charge on the basis of the light signal emitted by the first scintillator arranged on the polygonal matrix array.

Advantageously, at least one of the N conversion stages furthermore comprises a second scintillator arranged underneath the monolithic substrate of said at least one of the N conversion stages.

Advantageously, the digital detector according to the invention furthermore comprises a filter for filtering the low-energy incident radiation between the second scintillator of the at least one of the N conversion stages and the first scintillator of the lower conversion stage.

Advantageously, at least one pixel of the polygonal matrix array of pixels of at least one of the N conversion stages comprises photodiodes comprising two transparent electrodes.

Advantageously, the pixels of the polygonal matrix array of pixels of each of the N conversion stages comprise photodiodes comprising a transparent electrode and an opaque electrode, arranged alternately with a checkerboard arrangement in the polygonal matrix array of a conversion stage and with a checkerboard arrangement from one conversion stage to the adjacent conversion stage.

Advantageously, for at least one of the N conversion stages, the addressing and driving module for addressing and driving the matrix array is transferred directly onto the matrix array.

Advantageously, for said at least one of the N conversion stages, the polygonal matrix array comprises extensions bearing conductors connecting the addressing and driving module to the polygonal matrix array.

BRIEF DESCRIPTION OF THE DRAWINGS

The invention will be better understood and further advantages will become apparent from reading the detailed description of one embodiment provided by way of example, which description is illustrated by the attached drawing, in which.

For the sake of clarity, these figures are not all to the same scale. Moreover, the same elements will bear the same references in the various figures.

DETAILED DESCRIPTION

FIG. 1 schematically shows a traditional image detector. This was presented in the introduction.

Figure 2:
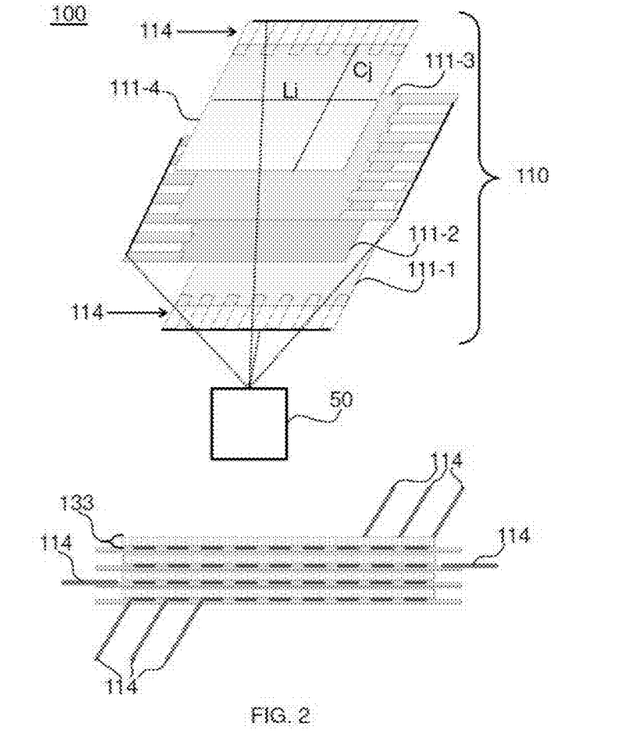
FIG. 2 schematically shows the principle of a digital detector with superposed conversion stages according to the invention.

FIG. 2 schematically shows the principle of a digital detector 100 with superposed conversion stages according to the invention. The digital detector 100 comprises a conversion block 110 intended to convert incident radiation into electric charge, and an electronic card 50 that converts the electric charge into a digital image. According to the invention, the conversion block 110 comprises N conversion stages 111-1, 111-2, 111-3, 111-4 superposed on one another. N is an integer between 2 and M, and preferably at least three. Each of the N conversion stages comprises a monolithic substrate 112, a first converter assembly 113 in the form of a polygonal matrix array, M being the number of sides of the polygonal matrix array, said matrix array being arranged on the monolithic substrate, and being organized in rows Li and columns Cj and configured so as to generate the electric charge on the basis of the incident radiation. Each of the N conversion stages furthermore comprises an addressing and driving module 114 for addressing and driving the matrix array, said addressing and driving module being arranged on the monolithic substrate 112 at the base of the columns Cj along one side of the polygonal matrix array, and intended to address the rows Li and transport the generated electric charge in the columns Cj. Each of the N conversion stages 111-1, 111-2, 111-3, 111-4 is oriented by at least 1/M of a turn with respect to the other N−1 conversion stages of the conversion block 110, and with an orientation distinct from the other N−1 conversion stages of the conversion block 110. In other words, the conversion stages are superposed on one another along a first axis, and each of the stages is oriented, about the first axis, by an angle equal to a multiple of 1/M, and such that the addressing and driving modules 114 for addressing and driving the matrix array of the N conversion stages are each distributed on one side of the conversion block.

The polygonal matrix array has M sides. M is preferably equal to 4, in which case the matrix array is rectangular (or square). The invention also applies to values other than M, under the proviso that the associated addressing and driving module 114 for addressing and driving the matrix array is arranged on one edge of the matrix, for example M equal to 3, 5, 6 or even more. Hereinafter, the invention will be described with a rectangular matrix array, that is to say with M equal to 4.

As shown in FIG. 2, the conversion block 110 comprises four conversion stages 111-1, 111-2, 111-3, 111-4. Each of the conversion stages is oriented by ¼ with respect to another conversion stage, and has a distinct orientation from the other three conversion stages. In other words, each edge of the conversion block has an associated single addressing and driving module 114 for addressing and driving the matrix array, even though the conversion block comprises four conversion stages.

The bottom of FIG. 2 shows the stack of conversion stages with the addressing and driving modules 114 for addressing and driving the matrix array. In this illustration, the conversion of the incident radiation into electric charge is performed by a scintillator and photodiodes. As an alternative, the conversion of incident radiation into electric charge may be obtained with a photodetector.

Advantageously, the matrix arrays of the conversion stages are formed on a thin substrate 112. A thin substrate is made of flexible plastic a few tens of micrometres thick. As mentioned above, in order for the driving and the addressing to be able to take place from a single side of the conversion block, the modules 114 are based on the technology known as "integrated drivers" for the driving (also known by the acronym GOA: Gate drivers On Array). It is thus possible to form stacks that may contain up to four matrix arrays of photodiodes and up to eight distinct layers of scintillators. It then becomes possible to separate the energy from the incident X-rays into multiple channels (potentially up to 8 in the example where M is equal to 4), while still improving the sensitivity and resolution of the assembly. Such modules 114 are described for example in the documents EP2708023B1 and EP3672230A1. These connector modules (for example of the type FPC: Flexible Printed Circuit, including an integrated readout circuit) may be assembled using the conventional flex technique with an anisotropic conductive film (ACF). One variant may be obtained by transferring the integrated readout circuits directly onto the same substrate using flip-chip technology and creating extensions to the substrate on an edge beyond these circuits. It is then possible to connect the matrix arrays directly to an electronic card with a simple ZIF connector or the like. This aspect will be described further below.

The invention thus makes it possible to form a stack of conversion stages that makes it possible to form a radiology image sensor with the capability of simultaneously producing images corresponding to various energies of the incident X-ray photons. It is possible to obtain up to eight energy channels without notably increasing the complexity of the assembly in comparison with products that are at present able to separate only high and low energy. The whole stack may be formed while complying with the dimensional constraints imposed for portable planar sensors.

This aspect is innovative since it makes it possible to overcome both the connection problems associated with a stack of conversion stages and to limit the absorption of X-rays in the substrates. On the contrary, it increases the overall absorption of the assembly, since multiple scintillators are superposed. Specifically, in the prior art, the issue of connecting the matrix arrays is seldom addressed, and there is no simple solution for connecting the driving circuits and the readout circuits at the periphery when the stack comprises more than two matrix arrays. Even though they are still possible from a theoretical point of view, stacks comprising more than three scintillators are difficult to produce without resorting to a complex and bulky architecture. In the prior art, when the number of matrix arrays exceeds two, it becomes necessary to have multiple rows of connectors on at least one side, this posing challenging problems for manufacturing and assembling the final product. In this case, it would be necessary to have interleaved or nested devices, which are incompatible with industrial production. This difficulty increases when portable detectors are involved, in which the constraints in terms of mass, thickness and lateral bulk are particularly strict. This difficulty dissuades a person skilled in the art from contemplating such a stack, which is synonymous with implementation complexity and greater bulk. In addition, stacking a large number of matrix arrays, which are usually formed on thick substrates, increases both the absorption of X-rays lost in the substrates and the lateral diffusion thereof, thereby leading to an intrinsic limitation on DQE (Detective Quantum Efficiency). In practice, modern architectures are therefore limited to obtaining dual-energy images (low and high energy), each channel being associated with a matrix array of the stack. The invention provides a solution to the prejudice according to which a stack of conversion stages means bulk and complexity of the connections and lateral diffusion of light between the layers and worsening of the resolution. The architecture of the detector according to the invention addresses these problems. The composite structure thus formed is able to be assembled easily in a sensor without providing any particular complexity in comparison with the case of a simple matrix array. Increasing the number of layers makes it possible to separate the total thickness of the scintillator into slices of thin thicknesses. The total thickness of these layers makes it possible to obtain high absorption, also denoted DQE(0), while still improving the MTF, in particular on the one or more first layers. It may also be contemplated to have pixels of different sizes and shapes depending on the layers in order to optimize overall performance (sensitivity, spatial resolution, spectral resolution) or to promote one of these features depending on the targeted application type.

Figure 3:
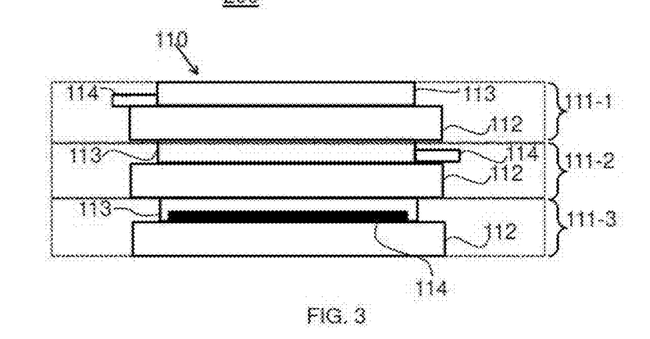
FIG. 3 schematically shows a first embodiment of a digital detector according to the invention.

FIG. 3 schematically shows a first embodiment of a digital detector 200 according to the invention. In this embodiment, the converter assemblies 113 are photodetectors, each of the photodetectors being able to absorb the incident radiation and to transform it into electric charge.

Figure 4:
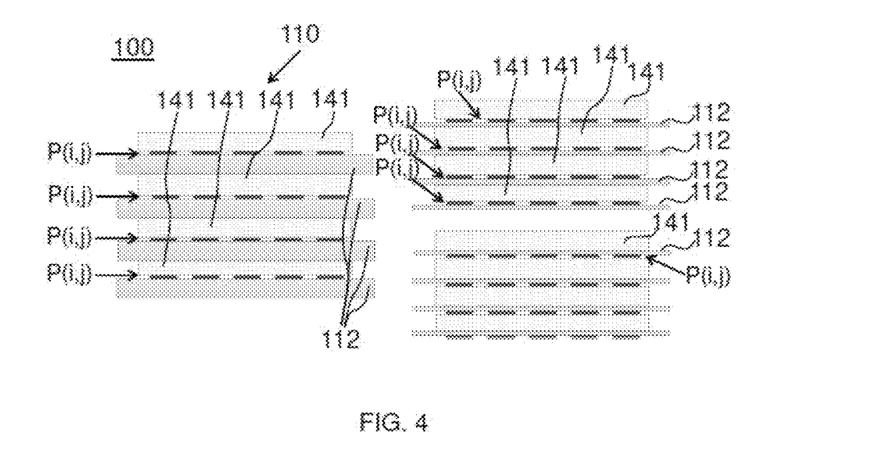
FIG. 4 schematically shows a second embodiment of a digital detector according to the invention.

FIG. 4 schematically shows a second embodiment of a digital detector 100 according to the invention. In this embodiment, each of said converter assemblies 133 comprises a first scintillator 141 able to convert the incident radiation into a light signal, and the polygonal matrix is a matrix array of pixels P(i,j) and configured so as to generate the electric charge on the basis of the light signal 19 emitted by the first scintillator 141 arranged on the polygonal matrix array.

Figure 5:
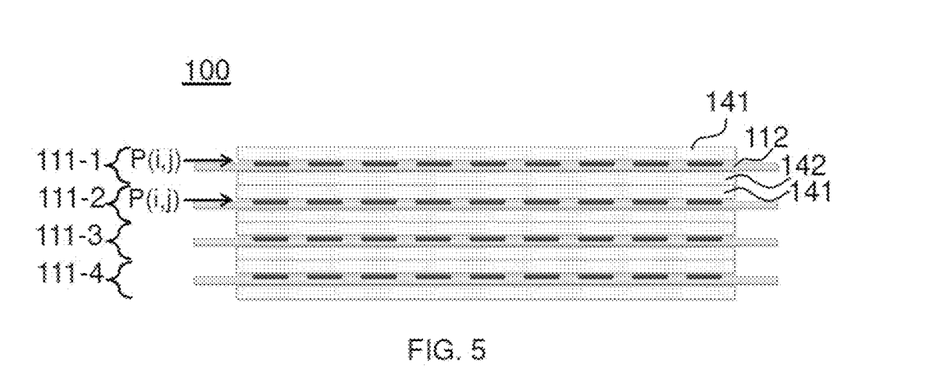
FIG. 5 schematically shows a third embodiment of a digital detector according to the invention.

FIG. 5 schematically shows a third embodiment of a digital detector 100 according to the invention. In this embodiment, at least one of the N conversion stages 111-1, 111-2, 111-3, 111-4 furthermore comprises a second scintillator 142 arranged underneath the monolithic substrate 112 of said at least one of the N conversion stages 111-1, 111-2, 111-3, 111-4.

In the example of FIG. 5, all of the conversion stages comprise a second scintillator 142 underneath the substrate 112. Each matrix array of photodiodes is associated with two scintillators. This structure may be advantageous if some or all of the photodiodes have two transparent electrodes, thus making it possible to maximize the efficiency of light collection.

This feature of the invention is also applicable if the converter assemblies are photodetectors. In such an embodiment, at least one of the N conversion stages 111-1, 111-2, 111-3, 111-4 then comprises a second converter assembly arranged underneath the monolithic substrate 112 of said at least one of the N conversion stages 111-1, 111-2, 111-3, 111-4.

Figure 6:
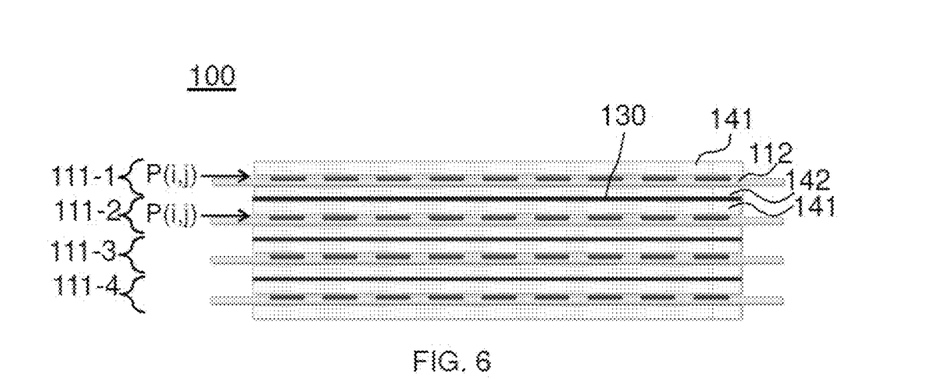
FIG. 6 schematically shows a fourth embodiment of a digital detector according to the invention.

FIG. 6 schematically shows a fourth embodiment of a digital detector 100 according to the invention. In this embodiment, the digital detector 100 furthermore comprises a filter 130 for filtering the predetermined-energy incident radiation between the second scintillator 142 of the at least one of the N conversion stages 111-1, 111-2, 111-3, 111-4 and the first scintillator 141 of the lower conversion stage. The energy level is between 20 and 150 keV. In the field of radiology, it is generally between 40 and 120 keV. The highest-energy photons (in the top part of the abovementioned ranges) access the deep layers of the conversion block, while the low-energy photons (in the bottom part of the abovementioned ranges) are absorbed in the first layers of the conversion block. The filter 130 is intended to filter the lowest-energy X-rays, thus making it possible to tighten the spectrum and increase selectivity between the successive layers. This tightening has the result of reducing the total absorption by the set of scintillating layers, but may exhibit an advantage when spectral selectivity is preferred to total sensitivity.

This feature of the invention is also applicable if the converter assemblies are photodetectors. In such an embodiment, the digital detector 200 furthermore comprises a filter 130 for filtering the predetermined-energy incident radiation between the second converter assembly of the at least one of the N conversion stages 111-1, 111-2, 111-3, 111-4 and the first converter assembly 113 of the lower conversion stage 111-1, 111-2, 111-3, 111-4.

Figure 7:
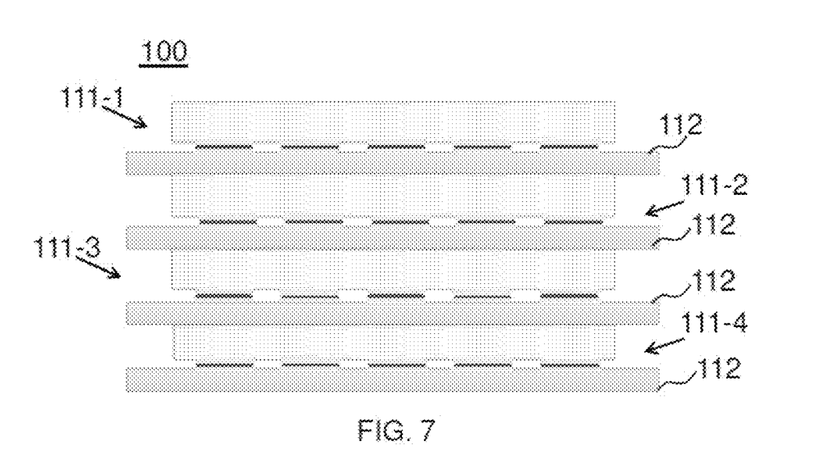
FIG. 7 schematically shows a fifth embodiment of a digital detector according to the invention.

FIG. 7 schematically shows a fifth embodiment of a digital detector 100 according to the invention. In this fifth embodiment, at least one pixel P(i,j) of the polygonal matrix array of pixels P(i,j) of at least one of the N conversion stages 111-1, 111-2, 111-3, 111-4 comprises photodiodes comprising two transparent electrodes. This embodiment has the advantage of maximizing the efficiency of collecting light emitted by the scintillators, since the photodiodes are able to receive visible photons through the top and through the bottom. The trade-off may be a decrease in spectral resolution (MFT), in particular if the transparent substrate layers are thick and allow lateral diffusion of light. It is therefore preferable to use substrates that are as thin as possible in order to limit this diffusion and also to reduce the absorption of X-rays, even though this absorption is generally low, of the order of a few percent.

Figure 8:
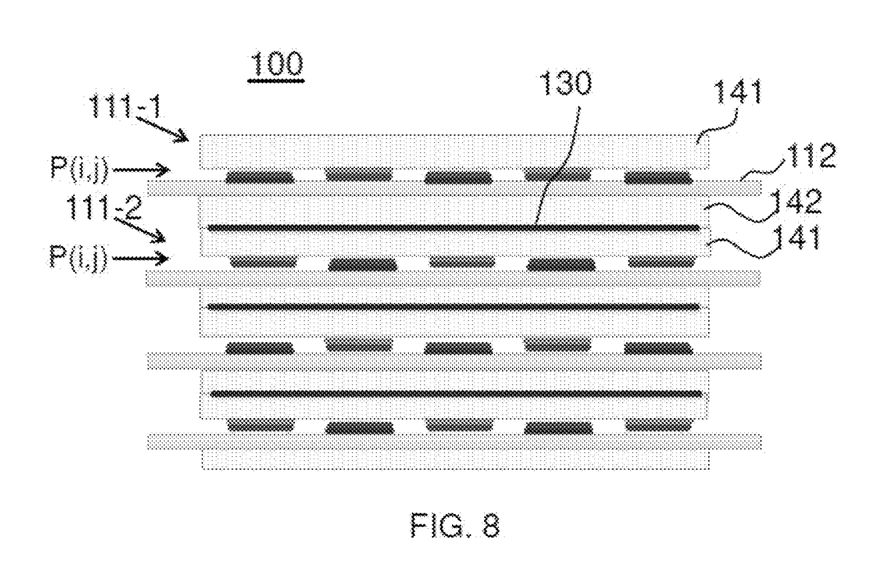
FIG. 8 schematically shows a sixth embodiment of a digital detector according to the invention.

FIG. 8 schematically shows a sixth embodiment of a digital detector 100 according to the invention. In this sixth embodiment, the pixels P(i,j) of the polygonal matrix array of pixels P(i,j) of each of the N conversion stages 111-1, 111-2, 111-3, 111-4 comprise photodiodes comprising a transparent electrode and an opaque electrode, arranged alternately with a checkerboard arrangement in the polygonal matrix array of a conversion stage and with a checkerboard arrangement from one conversion stage to the adjacent conversion stage (in FIG. 8, and as will be understood by a person skilled in the art upon reading this description, the light and dark lines represent the pixels and their opaque electrode). In other words, each matrix array comprises pixels in which one electrode is transparent and the other is opaque, this feature alternating with a checkerboard arrangement. This configuration makes it possible, on the same matrix array, for example for the stage 111-1, to collect the light emitted by the lower scintillator 142 with the pixels whose lower electrode is transparent and the light emitted by the upper scintillator 141 with the pixels whose upper electrode is transparent. By associating these checkerboard matrix arrays with eight scintillators, it is then possible to obtain a spectral image on eight energy channels. Optionally, the X-ray spectrum may advantageously be tightened with intermediate metal filters 130 in order to improve inter-channel selectivity, at the expense of less sensitivity.

The alternating transparency (front face/rear face) may optionally be implemented with non-square pixels, in order to recombine a dual-energy image with square pixels. For example, a low-energy rectangular pixel and a high-energy rectangular pixel are recombined into a single dual-energy square pixel equivalent to two colours. This "checkerboard"

alternation of pixels with a transparent front face and rear face may be applied generally to other geometric combinations that make it possible to alternate between these transparencies on the two faces, with for example an alternation of even/odd rows or columns or other possibly non-symmetric distributions.

In another embodiment of the invention, for at least one of the N conversion stages 111-1, 111-2, 111-3, 111-4, the addressing and driving module 114 for addressing and driving the matrix array may be transferred directly onto the matrix array. This embodiment may be combined with the other embodiments presented above.

Figure 9:
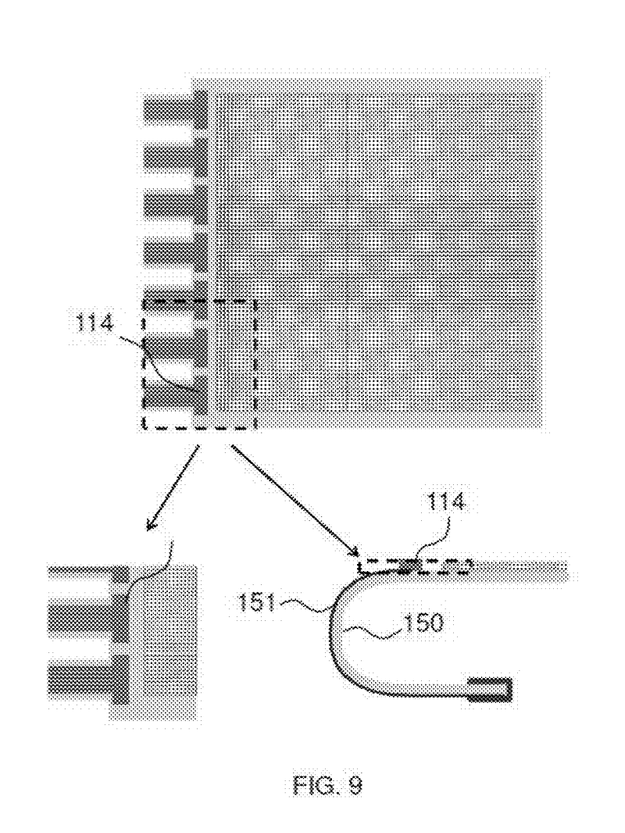
FIG. 9 schematically shows a seventh embodiment of a digital detector according to the invention.

FIG. 9 schematically shows a seventh embodiment of a digital detector according to the invention. In this embodiment, with the addressing and driving module 114 for addressing and driving the matrix array transferred directly onto the matrix array, for at least one of the N conversion stages 111-1, 111-2, 111-3, 111-4, and advantageously for all of the conversion stages, the polygonal matrix array comprises extensions 150 bearing conductors 151 connecting the addressing and driving module 114 to the polygonal matrix array.

In the case of the converter assembly comprising a scintillator and a matrix array of photodiodes, the polygonal matrix array of pixels P(i,j) comprises extensions 150 bearing conductors 151 connecting the addressing and driving module 114 for addressing and driving the pixels P(i,j) to the pixels P(i,j) of the polygonal matrix array of pixels P(i,j).

By virtue of directly transferring the readout circuits for reading out the signal emitted by the photodiodes, for example using "chip on flex" technology, it is no longer necessary to flex the flexible connectors bearing these circuits (FPC). This feature enables the direct connection of the matrix arrays of photodiodes by virtue of the formation in the same substrate of the extensions 150 that bear the conductors 151. The set of matrix arrays and scintillators that is extended by these flexible tabs may then be connected directly to an electronic card by way of ZIF connectors or the like, without it being necessary to perform a flexing operation on the electronic card.

It may be noted that this last feature of the invention is applicable within the scope of the invention. However, it may also apply to the case where the conversion block comprises only one conversion stage, that is to say without a matrix array stack.

The invention makes it possible to produce radiology image sensors with spectral selectivity ranging up to eight channels, while current systems are limited to two energy levels. The proposed stack, which combines a thin substrate, addressing using integrated drivers and possibly filters and advantageous combinations of photodiodes with opaque or transparent electrodes, makes it possible to produce these sensors in numerous variants with a reduced bulk that is compatible with the requirements for producing a portable detector. Depending on the variants chosen, it is possible to maximize X-ray absorption, spatial and spectral resolution of the image and selectivity between the various energies.

The applications of spectral imaging in radiology are currently limited to dual energy and to tomography (scanner). By virtue of the invention, the possibility of expanding spectral selectivity may open up significant fields for diagnostic quality by separating various tissues.

The invention is described in the field of radiology. However, industrial applications in terms of security and non-destructive testing are also significant, and the use of a multi-spectral planar sensor based on the invention could also advantageously replace linear sensor systems, for example for inspecting luggage in airports.

The invention claimed is:

1. A digital detector comprising:
   a conversion block intended to convert incident radiation into electric charge;
   an electronic card that converts the electric charge into a digital image, the conversion block comprising N conversion stages superposed on one another, N being an integer between 2 and M, each of the N conversion stages comprising:
   a monolithic substrate;
   a first converter assembly in the form of a polygonal matrix array, M being the number of sides of the polygonal matrix array, M being equal to 4, said matrix array being arranged on the monolithic substrate and being organized in rows (Li) and columns (Cj) and configured so as to generate the electric charge on the basis of the incident radiation;
   an addressing and driving module for addressing and driving the matrix array, said addressing and driving module being arranged entirely on the monolithic substrate at a base of the columns (Cj) along one side of the polygonal matrix array, and intended to address the rows (Li) and transport the generated electric charge in the columns (Cj);
   each of the N conversion stages being oriented by at least 1/M of a turn with respect to the other N−1 conversion stages of the conversion block, and with an orientation distinct from the other N−1 conversion stages of the conversion block,
   the digital detector being wherein each of said converter assemblies comprises a first scintillator able to convert the incident radiation into a light signal, and wherein the polygonal matrix is a matrix array of pixels (P(i,j)) and configured so as to generate the electric charge on the basis of the light signal emitted by the first scintillator arranged on the polygonal matrix array, and in that at least one of the N conversion stages furthermore comprises a second scintillator arranged underneath the monolithic substrate of said at least one of the N conversion stages.

2. The digital detector according to claim 1, wherein said converter assemblies are photodetectors, each of the photodetectors being able to absorb the incident radiation and to transform it into electric charge.

3. The digital detector according to claim 2, wherein at least one of the N conversion stages furthermore comprises a second converter assembly arranged underneath the monolithic substrate of said at least one of the N conversion stages.

4. The digital detector according to claim 3, furthermore comprising a filter for filtering the predetermined-energy incident radiation between the second converter assembly of the at least one of the N conversion stages and the first converter assembly of the lower conversion stage.

5. The digital detector according to claim 1, furthermore comprising a filter for filtering the low-energy incident radiation between the second scintillator of the at least one of the N conversion stages and the first scintillator of the lower conversion stage.

6. The digital detector according to claim 1, wherein at least one pixel (P(i,j)) of the polygonal matrix array of pixels (P(i,j)) of at least one of the N conversion stages comprises photodiodes comprising two transparent electrodes.

7. The digital detector according to claim 1, wherein the pixels (P(i,j)) of the polygonal matrix array of pixels (P(i,j)) of each of the N conversion stages comprise photodiodes comprising a transparent electrode and an opaque electrode, arranged alternately with a checkerboard arrangement in the polygonal matrix array of a conversion stage and with a checkerboard arrangement from one conversion stage to the adjacent conversion stage.

8. The digital detector according to claim 1, wherein, for at least one of the N conversion stages, the addressing and driving module for addressing and driving the matrix array is transferred directly onto the matrix array.

9. The digital detector according to claim 8, wherein, for said at least one of the N conversion stages, the polygonal matrix array comprises extensions bearing conductors connecting the addressing and driving module to the polygonal matrix array.

\* \* \* \* \*